(12) United States Patent
Zhang

(10) Patent No.: US 8,889,650 B2
(45) Date of Patent: *Nov. 18, 2014

(54) ANTIMELANCHOLIC MEDICINE PREPARED WITH JUJUBE CAMP MATERIALS

(75) Inventor: Zuoguang Zhang, Beijing (CN)

(73) Assignees: Beijing Wonner Biotech, Ltd. Co., Beijing (CN); Zuoguang Zhang, Beijing (CN); Yu-Fen Chi, New Taipei (TW)

( * ) Notice: Subject to any disclaimer, the term of this patent is extended or adjusted under 35 U.S.C. 154(b) by 97 days.

This patent is subject to a terminal disclaimer.

(21) Appl. No.: 12/745,438

(22) PCT Filed: Nov. 30, 2007

(86) PCT No.: PCT/CN2007/003397
§ 371 (c)(1),
(2), (4) Date: Aug. 23, 2010

(87) PCT Pub. No.: WO2009/070921
PCT Pub. Date: Jun. 11, 2009

(65) Prior Publication Data
US 2010/0311682 A1    Dec. 9, 2010

(51) Int. Cl.
| | | |
|---|---|---|
| A01N 43/04 | (2006.01) |
| A61K 31/70 | (2006.01) |
| C07G 3/00 | (2006.01) |
| C07G 11/00 | (2006.01) |
| C07H 15/00 | (2006.01) |
| C07H 17/00 | (2006.01) |
| C07H 19/20 | (2006.01) |
| B01J 20/286 | (2006.01) |
| A61K 9/20 | (2006.01) |
| B01J 20/28 | (2006.01) |
| A61K 36/725 | (2006.01) |
| B01D 15/08 | (2006.01) |
| B01J 20/32 | (2006.01) |
| A61K 31/7076 | (2006.01) |

(52) U.S. Cl.
CPC ........... *A61K 31/7076* (2013.01); *B01J 20/286* (2013.01); *A61K 9/2059* (2013.01); *B01J 20/28085* (2013.01); *A61K 36/725* (2013.01); *B01D 15/08* (2013.01); *B01J 20/3248* (2013.01); *B01J 20/3208* (2013.01)
USPC ............................ 514/47; 536/4.1; 536/26.13

(58) Field of Classification Search
CPC ............ A61K 9/2059; A61K 31/7076; A61K 36/725; B01J 20/3248; B01J 20/28085; B01J 20/286; B01J 20/3208; B01D 15/08
See application file for complete search history.

(56) References Cited

U.S. PATENT DOCUMENTS

| | | | | |
|---|---|---|---|---|
| 6,395,311 B2 * | 5/2002 | Jia | .................................. | 424/744 |
| 2009/0232914 A1 * | 9/2009 | Zhang | .......................... | 424/728 |

OTHER PUBLICATIONS (R) Anon., Sigma Catalog, Biochemical and Reagents for Life Science Research, St. Louis, MO, 2002-2003, only p. 76, cols. 1-2, cAMP and salts thereof in four entries—see entries A9501-A3262.*
(S) M. J. O'Neil et al. (eds.), "The Merck Index, 13th Edition," Merck & Co., Whitehouse Station, NJ, 2001, only pp. 471 supplied (see "Cyclic AMP").*
(T) Lehninger, A. L., "Biochemistry, 2nd Edition, The Molecular Basis of Cell Structure and Function," Worth Publisheres, Inc., New York, N.Y., 1975, only p. 812 supplied (see references to the hydrolysis of "cAMP").*
Li et al., "Extract Process of Cyclic Adenosinemonophosphate (cAMP) in *Ziziphus jujuba*," Journal of Chinese Medicinal Materials (2007) 30(9):1143-1145.

* cited by examiner

*Primary Examiner* — Lawrence E Crane
(74) *Attorney, Agent, or Firm* — Volpe and Koenig, P.C.

(57) ABSTRACT

An antimelancholic pharmaceutical composition or health products prepared with jujuba cAMP materials and a preparative method are provided in the present invention. The present pharmaceutical composition includes jujuba cAMP as a solo effective ingredient for treating the depression. The present method for preparing the jujuba cAMP includes chromatographing a jujuba extract with a macroporous resin bound with an aldehyde group.

3 Claims, 7 Drawing Sheets

ANTIMELANCHOLIC MEDICINE PREPARED WITH JUJUBE CAMP MATERIALS

CROSS-REFERENCE TO RELATED APPLICATION AND CLAIM OF PRIORITY

The application claims the benefit of PCT Patent Application No. PCT/CN07/03397, filed on Nov. 30, 2007, in the State Intellectual Property Office of the P.R.C., the disclosures of which are incorporated herein in their entirety by reference.

FIELD OF THE INVENTION

The present invention relates to a medicine or a healthcare product prepared from jujuba cyclic adenosine monophosphate (jujuba cAMP) material for treating depression (melancholia). Furthermore, the present invention relates to a preparation method of the medicine or the healthcare product from the jujuba cAMP material for treating depression.

BACKGROUND OF THE INVENTION

Depression is a common disease. According to statistics, about 25% females in the global population bad been experiencing depression in their lives, and about 10% males had been experiencing depression (referring to *Modern Psychology* written by Ch'un-Hsing Chang). World Health Organization (WHO) published, "The incidence of depression in the world is about 11%. At present, there are about 340 million psychological depressed patients in the world, and the number is increasing. It is found in the investigation that depression will increase to be the number two common disease in the world from now on to 20 years later."

At present, anti-depression pharmaceuticals consist mainly Prozac, Paxil and Zoloft, etc., which belong to selective serotonin reuptake inhibitor (SSRI), serotonin-norepinephrine reuptake inhibitor (SNRT), and norepinephrine and dopamine reuptake inhibitor (NDRI), inhibiting the uptake of 5-hydroxytryptamine (5-HT), norepinephrine (NE) and dopamine (DA). The mechanism by which these pharmaceuticals function is by increasing the amount of human neurotransmitters such as 5-HT so as to decrease and alleviate the symptoms of depression.

However, these pharmaceuticals have various side effects of different severities, such as increased suicide rate, headache, giddiness, vertigo, insomnolence, hypersomnia, tinnitus, thirsty, apocleisis, orexis, increased body weight, increased blood pressure, stomach upset, regurgitation nausea, emesis, dyspepsia, diarrhea, constipation, leg pain, skin rash, dither, convulsions, hyperhidrosis, edema, sexual appetite, impotence, etc. In recent years, the depression pharmaceuticals, such as Prozac, etc., had become a serious social problem. In 2004, the Food and Drug Administration (FDA) of the United States further mandated the pharmaceutical companies to revise product labels to clearly state the side effects and cautions in the instructions of 32 major anti-depression pharmaceuticals in the market, and emphasized to physicians and nurses that these pharmaceuticals might increase children's and adolescents' suicide rate. Among them, Paxil was even found to be harmful in 1996, and has been recalled continually from the market since 2001. In June 2004, the New York State Attorney General accused Glaxo-SmithKline Company of the Great Britain of beguilingly concealing the research report of the linkage between Paxil and "increased risk of suicidal behavior and tendencies in adolescents." In light of the current situation, the search for a new generation of pharmaceuticals with fewer side effects and more pronounced/potent anti-depression qualities has become the center of attention of the entire pharmaceutical world.

It is therefore attempted by the applicant to deal with the above situation encountered in the prior art.

SUMMARY OF THE INVENTION

The purpose of the present invention is to provide a medicine or a healthcare product prepared from material containing jujuba cAMP for treating depression to overcome the insufficiency of the present technology. In particular, the invention provides new technical schemes that avoid the side effects of the present anti-depression medicine.

Another purpose of the present invention is to provide the preparation method of the medicine or the healthcare product from the material containing jujuba cAMP for treating depression.

The resolving scheme of the pharmaceutical of the present invention is the result of substantial efforts of the inventor. The resolving scheme combines the theories of modern medicine and pharmacology. In particular, the resolving scheme combines the research fields of adenylate cyclase (AC)—cyclic adenosine monophosphate (cAMP) signaling transduction pathway, the cAMP-inducing transcription process, and more. The inventor has been dedicated to the research of traditional botanical materials for treating depression. After much animal experimentation, jujuba cAMP, being the extrinsic non-hydrolyzable cAMP, which is known to the skilled person in the field, can participate in the cAMP metastatic process of the organism, and simulate the enzyme function to increase cAMP in the cells, and thus achieves the anti-depression effect. Jujuba cAMP is extracted from the daily edible fruit, jujuba. The cAMP isolated from a jujuba extraction is the proportion of cAMP originally present prior to extraction and which survived the isolation process because it was not hydrolyzed by the conditions applied during the isolation process. In the long history of human daily consumption of jujuba as fruit and as Chinese herbal medicine materials, there has been no case of a harmful reaction associated with taking jujuba, in contrast to the present anti-depression pharmaceuticals that have many undesirable side effects. After the inventor extracted jujuba containing a trace amount of jujuba cAMP (about one in ten thousand) by water, the inventor further purified the jujuba water extract into the jujuba extract containing 1% of jujuba cAMP. The jujuba extract thus processed was tested in the animal experiments for anti-experimental depression function, and the results demonstrate that the jujuba extract has an anti-experimental depression function. In contrast, the jujuba water extract that was not further purified to increase the concentration of jujuba cAMP, while containing a trace amount of jujuba cAMP, did not have an obvious anti-experimental depression function when the normal pharmaceutical dose was proceeded in the animal experiment testing for the anti-experimental depression function. Therefore, the invention submits the new technical scheme of manufacturing a pharmaceutical from the raw material of jujuba cAMP for treating depression, so as to improve the insufficiency in the prior art.

Jujuba cAMP:

Source: the dried matured fruit of *Zizyphus jujuba* Mill.

Synonym: 3',5'-cyclic adenosine monophosphate or 3',5'-cyclic phosphate.

English name: cyclic adenosine-3',5'-monophosphate.

Molecular formula and relative molecular weight: $C_{10}H_{13}N_5O_6P \cdot H_2O$ and 347.23 respectively.

Biological activity: The activity of cAMP-like material in jujuba is similar with that of cAMP. cAMP being the extrinsic non-hydrolyzable cAMP can simulate the enzyme function to increase cAMP in the cells.

Structural formula:

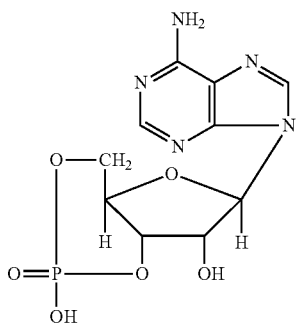 [SMILES: Nc1ncnc2c1ncn2C1OC2COP(=O)(O)COC2C1O]

In accordance with one aspect of the present invention, a medicine for treating depression is provided. The medicine includes jujuba cAMP.

Preferably, the medicine is manufactured as an oral medicine.

Preferably, the medicine has a dosage form being one selected from a group consisting of a tablet, a capsule, a powder, a pill, a dust, a solution, a microcapsule, a suspension, an emulsion, a particle, a dropping pill and a roll.

Preferably, the dosage form is a first oral dosage form for taking once per day and has 0.003 mg to 0.3 mg of jujuba cAMP. Preferably, the first oral dosage form has 0.01 mg to 0.25 mg of jujuba cAMP.

Preferably, the dosage form is a second oral dosage form for taking twice per day and has 0.002 mg to 0.2 mg of jujuba cAMP. Preferably, the second oral dosage form has 0.005 mg to 0.12 mg of jujuba cAMP.

Preferably, the dosage form is a third oral dosage form for taking thrice per day and has 0.001 mg to 0.1 mg of jujuba cAMP. Preferably, the third oral dosage form has 0.003 mg to 0.08 mg of jujuba cAMP.

Preferably, the dosage form is a fourth oral dosage form for taking four times per day and has 0.0008 mg to 0.06 mg of jujuba cAMP. Preferably, the fourth oral dosage form has 0.002 mg to 0.04 mg of jujuba cAMP.

Preferably, the medicine according to claim 1 further includes at least one of a pharmacologically acceptable carrier and an additive.

Preferably, the medicine is manufactured as a healthcare product or a nutrient supplement.

Preferably, jujuba cAMP is extracted from jujuba.

Preferably, jujuba is extracted for obtaining a first extract having a first jujuba cAMP concentration, the first extract is further extracted for obtaining a second extract having a second jujuba cAMP concentration, the second jujuba cAMP concentration is higher than the first jujuba cAMP concentration, and the second extract is a raw material in the medicine.

In accordance with another aspect of the present invention, a preparation method of jujuba cAMP of a medicine for treating depression is provided. The preparation method comprises steps of (a) extracting jujuba for obtaining a first extract having a first jujuba cAMP concentration; and (b) purifying the first extract for obtaining a second extract having a second jujuba cAMP concentration. The second jujuba cAMP concentration is higher than the first jujuba cAMP concentration.

Preferably, the step (b) is processed by chromatographing the first extract with a macroporous resin bound with an aldehyde group.

Preferably, the step (b) further comprises steps of (b1) chromatographing the first extract with an OU-2 macroporous resin bound with the aldehyde group; and (b2) chromatographing the first extract with an ME-2 macroporous resin bound with the aldehyde group.

In accordance with another aspect of the present invention, a method for preparing jujuba cAMP is provided. The method includes steps of (a) extracting jujuba for obtaining a first extract; and (b) chromatographing the first extract with a macroporous resin having an aldehyde group bound thereon.

The above objectives and advantages of the present invention will become more readily apparent to those ordinarily skilled in the art after reviewing the following detailed descriptions and accompanying drawings, in which:

DETAILED DESCRIPTION OF THE PREFERRED EMBODIMENT

Figure 1:
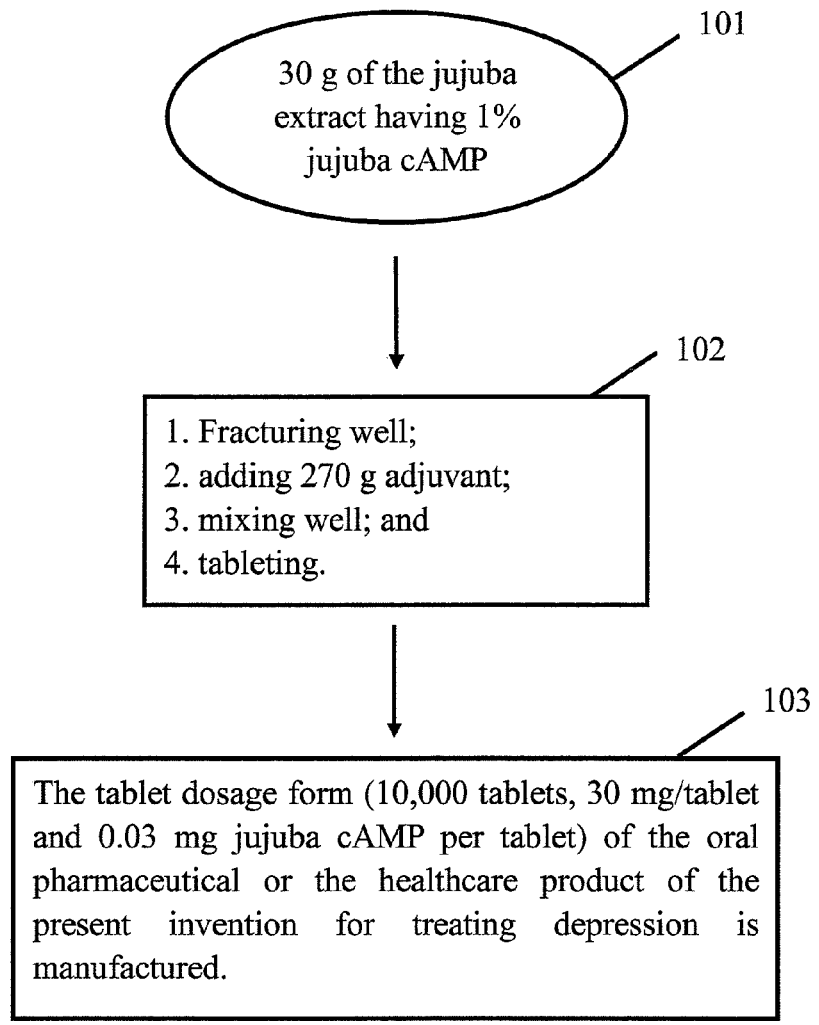
FIG. 1 is a flowchart showing a preparation method of a medicine in accordance with a first preferred embodiment of the present invention.

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

In order to accomplish the purpose of the present invention, the technical schemes of the present invention are particularly provided as follows.

EXAMPLE 1

The oral medicine of the present invention for treating depression was manufactured from the material including jujuba cAMP.

EXAMPLE 2

The raw material including jujuba cAMP was manufactured as any pharmacologically common oral medicine dosage form of the present invention, such as tablet, capsule, powder, pill, dust, solution, microcapsule, suspension, emulsion, particle, dropping pill, roll, etc., for treating depression.

EXAMPLE 3

The pharmaceutical of the present invention was manufactured from the raw material including 0.003~0.3 mg of jujuba cAMP as a dosage form for taking once per day. Preferably, the pharmaceutical of the present invention was manufactured from the raw material including 0.01~0.25 mg of jujuba cAMP as a dosage form for taking once per day.

EXAMPLE 4

The pharmaceutical of the present invention was manufactured from the raw material including 0.002~0.2 mg of jujuba cAMP as a dosage form for taking twice per day. Preferably, the pharmaceutical of the present invention was manufactured from the raw material including 0.005~0.12 mg of jujuba cAMP as a dosage form for taking twice per day.

EXAMPLE 5

The pharmaceutical of the present invention was manufactured from the raw material including 0.001~0.1 mg of jujuba cAMP as a dosage form for taking thrice per day. Preferably, the pharmaceutical of the present invention was manufactured from the raw material including 0.003~0.08 mg of jujuba cAMP as a dosage form for taking thrice per day.

EXAMPLE 6

The pharmaceutical of the present invention was manufactured from the raw material including 0.0008~0.06 mg of jujuba cAMP as a dosage form for taking four times per day. Preferably, the pharmaceutical of the present invention was manufactured from the raw material including 0.002~0.04 mg of jujuba cAMP as a dosage form for taking four times per day.

EXAMPLE 7

After jujuba was fractured, the fractured jujuba was soaked in the water at room temperature, and then the soaked jujuba underwent decoction and alcohol sedimentation for obtaining the jujuba extract, which was further absorbed, sequentially separated by the OU-2 and ME-2 macroporous resins and dried. Finally, the jujuba extract containing high concentration of jujuba cAMP was obtained to be the raw material for preparing the pharmaceutical of the present invention.

EXAMPLE 8

The oral medicine of the present invention can include the pharmacologically acceptable carriers, additives and the composition thereof.

EXAMPLE 9

The oral medicine of the present invention can be further manufactured as healthcare product and nutrient supplements.

In order to accomplish the purpose of the present invention, the preparation methods of the pharmaceutical is provided as follows.

Method 1:
In accordance with the pharmaceutical standard method of Good Manufacturing Practice (GMP), the oral medicine of the present invention for treating depression was manufactured from the raw material including jujuba cAMP.

Method 2:
In accordance with the pharmaceutical standard method of GMP, the raw material including jujuba cAMP was manufactured as any pharmacologically common oral medicine dosage form of the present invention, such as tablet, capsule, powder, pill, dust, solution, microcapsule, suspension, emulsion, particle, dropping pill, roll, etc., for treating depression.

Method 3:
In accordance with the pharmaceutical standard method of GMP, the pharmaceutical of the present invention was manufactured from the raw material including 0.003~0.3 mg of jujuba cAMP as a dosage form for taking once per day. Preferably, the pharmaceutical of the present invention was manufactured from the raw material including 0.01~0.25 mg of jujuba cAMP as a dosage form for taking once per day.

Method 4:
In accordance with the pharmaceutical standard method of GMP, the pharmaceutical of the present invention was manufactured from the raw material including 0.002~0.2 mg of jujuba cAMP as a dosage form for taking twice per day. Preferably, the pharmaceutical of the present invention was manufactured from the raw material including 0.005~0.12 mg of jujuba cAMP as a dosage form for taking twice per day.

Method 5:
In accordance with the pharmaceutical standard method of GMP, the pharmaceutical of the present invention was manufactured from the raw material including 0.001 ~0.1 mg of jujuba cAMP as a dosage form for taking thrice per day. Preferably, the pharmaceutical of the present invention was manufactured from the raw material including 0.003~0.08 mg of jujuba cAMP as a dosage form for taking thrice per day.

Method 6:
In accordance with the pharmaceutical standard method of GMP, the pharmaceutical of the present invention was manufactured from the raw material including 0.0008~0.06 mg of jujuba cAMP as a dosage form for taking four times per day. Preferably, the pharmaceutical of the present invention was manufactured from the raw material including 0.002~0.04 mg of jujuba cAMP as a dosage form for taking four times per day.

Method 7:
In accordance with the pharmaceutical standard method of GMP, after jujuba was fractured, the fractured jujuba was soaked in the water at room temperature, and then the soaked jujuba was extracted by decoction and alcohol sedimentation for obtaining the jujuba extract, which was further absorbed, sequentially separated by the OU-2 and ME-2 macroporous resins and dried. Finally, the jujuba extract containing high concentration of jujuba cAMP was obtained to be the raw material for preparing the pharmaceutical of the present invention.

Method 8:
In accordance with the pharmaceutical standard method of GMP, the oral medicine of the present invention can include the pharmacologically acceptable carriers, additives and the composition thereof.

Method 9:
In accordance with the pharmaceutical standard method of GMP, the oral medicine of the present invention can be further manufactured as healthcare product and nutrient supplements.

THE PREFERRED EMBODIMENT

The present invention is further illustrated as follows by combining the figures and the preferred embodiments.

Embodiment 1

Please refer to FIG. 1, which is the flowchart showing a preparation method of a medicine in accordance with a first preferred embodiment of the present invention. In FIG. 1, in accordance with the pharmaceutical standard method of GMP, 30 g of the prepared jujuba extract having 1% jujuba cAMP was the raw material (step 101). Two hundred seventy (270) g of the adjuvant and the excipient (such as starch, lactose, silicon dioxide and magnesium stearate, etc.) were added to manufacture the tablet dosage form (10,000 tablets, 30 mg/tablet and 0.03 mg jujuba cAMP per tablet) of the oral medicine or the healthcare product of the present invention for treating depression (steps 102 and 103).

Embodiment 2

Figure 2:
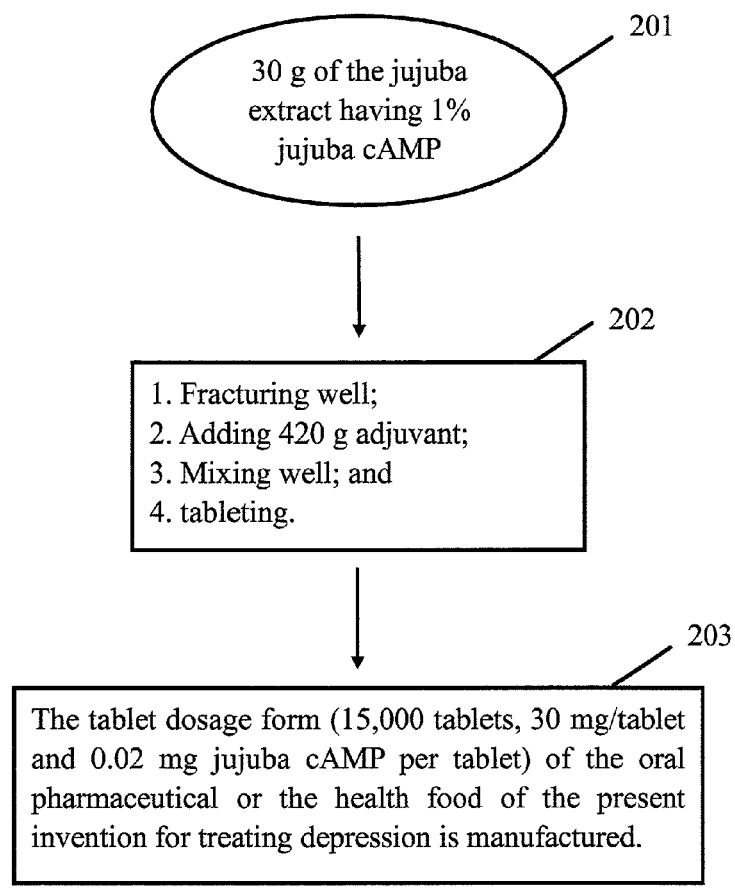
FIG. 2 is a flowchart showing a preparation method of a medicine in accordance with a second preferred embodiment of the present invention.

Please refer to FIG. 2, which is the flowchart showing a preparation method of a medicine in accordance with a second preferred embodiment of the present invention. In FIG. 2, in accordance with the pharmaceutical standard method of GMP, 30 g of the prepared jujuba extract having 1% jujuba cAMP was the raw material (step 201). Four hundred twenty (420) g of the adjuvant and the excipient (such as starch, lactose, silicon dioxide and magnesium stearate, etc.) were added to manufacture the tablet dosage form (15,000 tablets, 30 mg/tablet and 0.02 mg jujuba cAMP per tablet) of the oral medicine or the healthcare product of the present invention for treating depression (steps 202 and 203).

Embodiment 3

Figure 3:
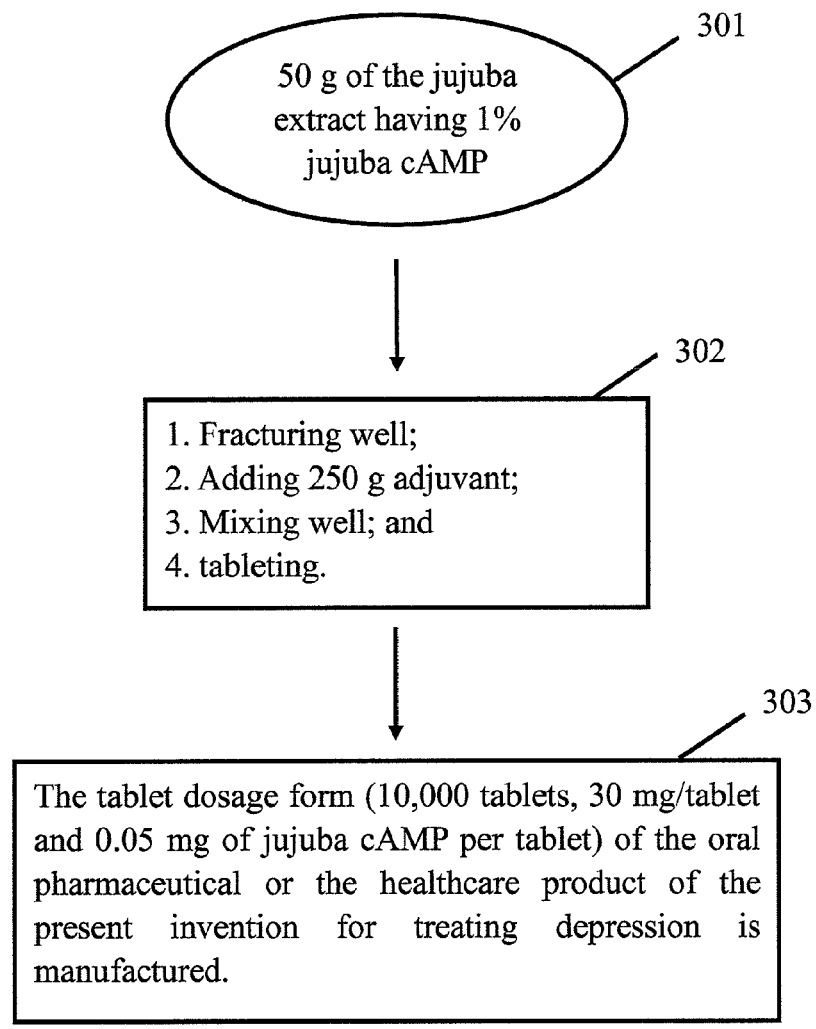
FIG. 3 is a flowchart showing a preparation method of a medicine in accordance with a third preferred embodiment of the present invention.

Please refer to FIG. 3, which is the flowchart showing a preparation method of a medicine in accordance with a third preferred embodiment of the present invention. In FIG. 3, in accordance with the pharmaceutical standard method of GMP, 50 g of the prepared jujuba extract having 1% jujuba cAMP was the raw material (step 301). Two hundred fifty (250) g of the adjuvant and the excipient (such as starch, lactose, silicon dioxide and magnesium stearate, etc.) were added to manufacture the tablet dosage form (10,000 tablets, 30 mg/tablet and 0.05 mg jujuba cAMP per tablet) of the oral medicine or the healthcare product of the present invention for treating depression (steps 302 and 303).

Embodiment 4

Figure 4:
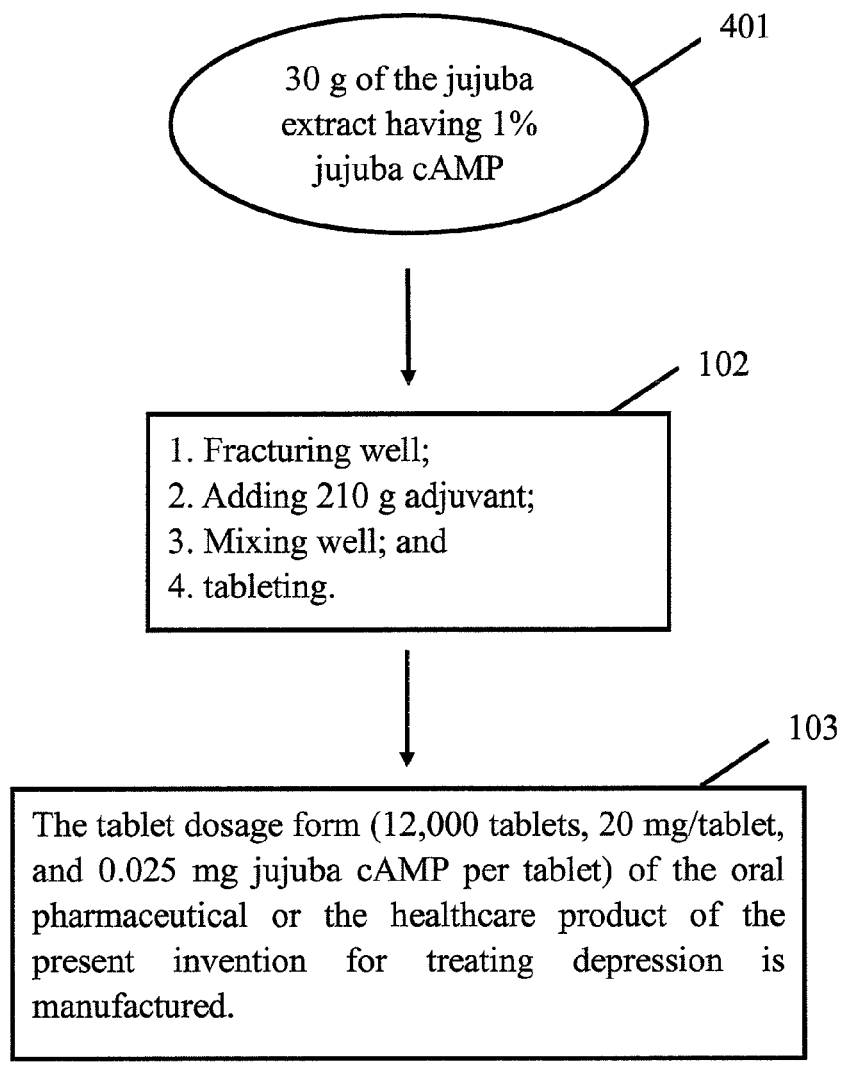
FIG. 4 is a flowchart showing a preparation method of a medicine in accordance with a fourth preferred embodiment of the present invention.

Please refer to FIG. 4, which is the flowchart showing a preparation method of a medicine in accordance with a fourth preferred embodiment of the present invention. In FIG. 4, in accordance with the pharmaceutical standard method of GMP, 30 g of the prepared jujuba extract having 1% jujuba cAMP was the raw material (step 401). Two hundred ten (210) g of the adjuvant and the excipient (such as starch, lactose, silicon dioxide and magnesium stearate, etc.) were added to manufacture the tablet dosage form (12,000 tablets, 20 mg/tablet and 0.25 mg jujuba cAMP per tablet) of the oral medicine or the health food of the present invention for treating depression (steps 402 and 403).

Embodiment 5

Figure 5:
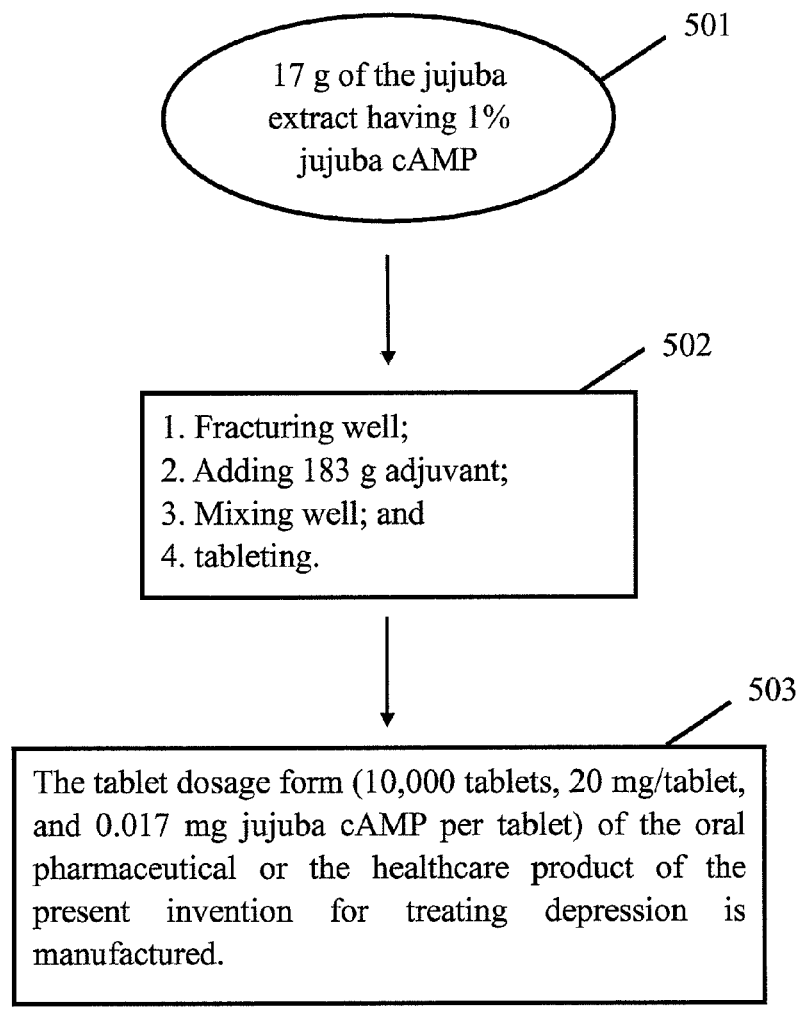
FIG. 5 is a flowchart showing a preparation method of a medicine in accordance with a fifth preferred embodiment of the present invention.

Please refer to FIG. 5, which is the flowchart showing a preparation method of a medicine in accordance with a fifth preferred embodiment of the present invention. In FIG. 5, in accordance with the pharmaceutical standard method of GMP, 17 g of the prepared jujuba extract having 1% jujuba cAMP was the raw material (step 501). One hundred eighty three (183) g of the adjuvant and the excipient (such as starch, lactose, silicon dioxide and magnesium stearate, etc.) were added to manufacture the tablet dosage form (10,000 tablets, 20 mg/tablet and 0.17 mg jujuba cAMP per tablet) of the oral medicine or the healthcare product of the present invention for treating depression (steps 502 and 503).

Embodiment 6

Figure 6:
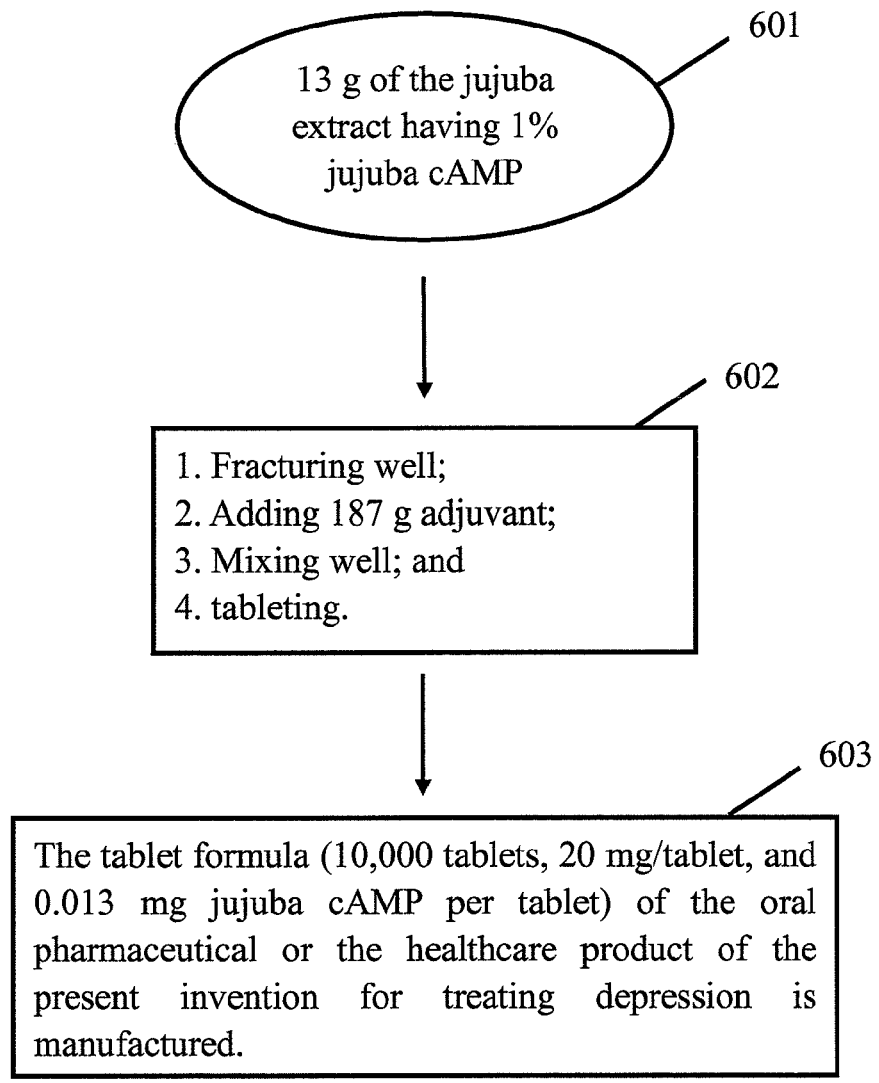
FIG. 6 is a flowchart showing a preparation method of a medicine in accordance with a sixth preferred embodiment of the present invention.

Please refer to FIG. 6, which is the flowchart showing a preparation method of a medicine in accordance with a sixth preferred embodiment of the present invention. In FIG. 6, in accordance with the pharmaceutical standard method of GMP, 13 g of the prepared jujuba extract having 1% jujuba cAMP was the raw material (step 601). One hundred eighty seven (187) g of the adjuvant and the excipient (such as starch, lactose, silicon dioxide and magnesium stearate, etc.) were added to manufacture the tablet dosage form (10,000 tablets, 20 mg/tablet, and 0.013 mg jujuba cAMP per tablet) of the oral medicine or the healthcare product of the present invention for treating depression (steps 602 and 603).

Embodiment 7

Figure 7:
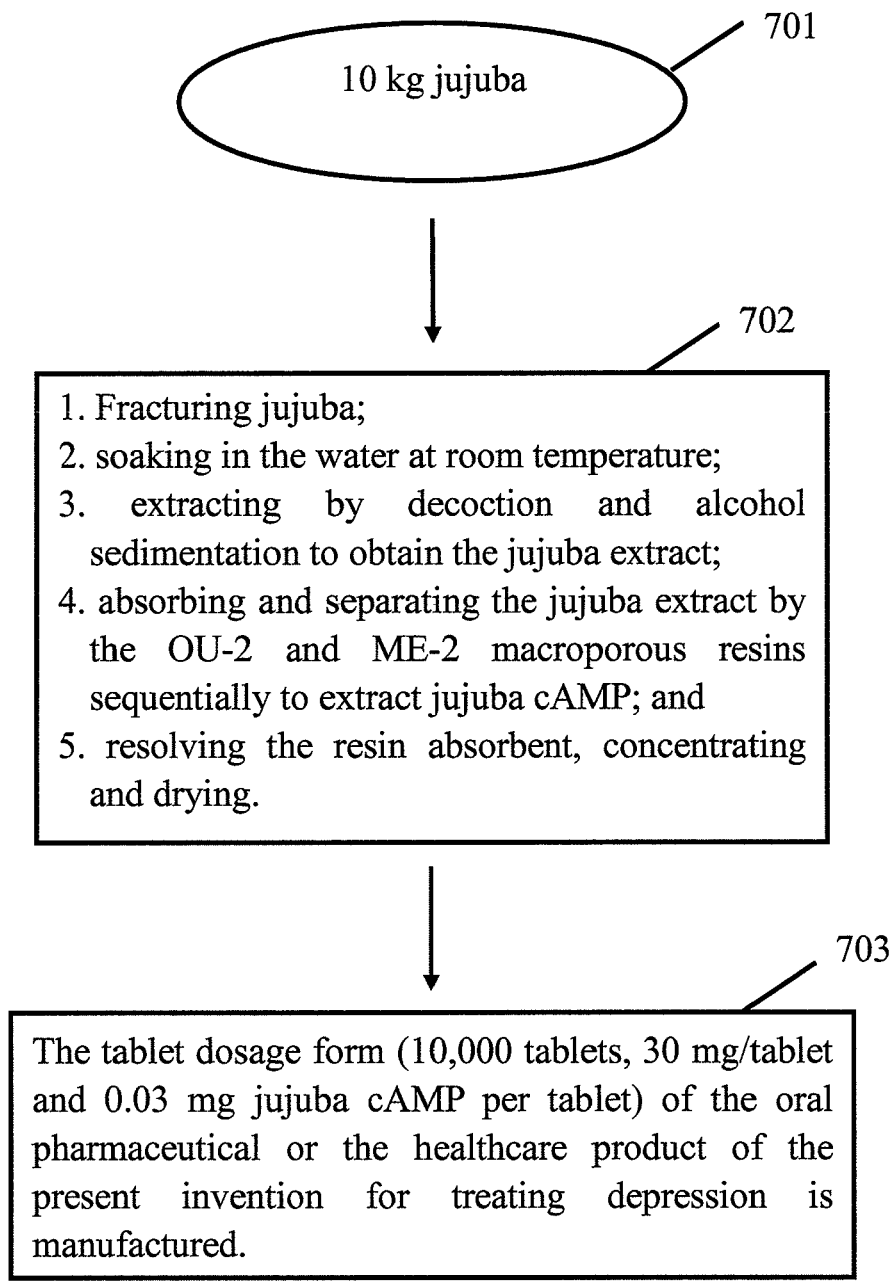
FIG. 7 is a flowchart showing a preparation method of a medicine in accordance with a seventh preferred embodiment of the present invention.

Please refer to FIG. 7, which is the flowchart showing a preparation method of a medicine in accordance with a seventh preferred embodiment of the present invention. In FIG. 7, in accordance with the pharmaceutical standard method of GMP, after 10 kg jujuba (step 701) was fractured, the fractured jujuba was soaked in the water at room temperature, and then the soaked jujuba was extracted by decoction and alcohol sedimentation for obtaining the jujuba extract, which was further absorbed, sequentially separated by the OU-2 and ME-2 macroporous resins and dried, so as to obtain 30 g of the jujuba extract having jujuba cAMP (step 702). The jujuba extract having 1% (300 mg) jujuba cAMP was measured by high performance liquid chromatography (HPLC), so as to manufacture the oral medicine or the healthcare product of the present invention for treating depression (step 703).

Experiment 1: The Influence of Embodiment 3 in the Mouse Tail-Hanging Experiment 1.1 Experimental animals: ICR mice, male, 22.0±2 g of body weight, secondary, were provided by the Experimental Animal Science Department of Capital Medical University, Beijing.

1.2 Experiment pharmaceuticals: The pharmaceutical of Embodiment 3 was provided by Beijing Wonner Biotech. Ltd. Co., and Paroxetine (Paxil) was the product of Zhong Mei Tianjin Smith Kline pharmaceuticals Co. Ltd.

1.3 Experimental equipment: Stop watch.

1.4 Dose designs: 1. High dose of Embodiment 3 (5 mg/kg/d); 2. middle dose of Embodiment 3 (2.5 mg/kg/d); and 3. low dose of Embodiment 3 (1.25 mg/kg/d).

1.5 Experimental method and result:

1.5.1 Group division and administration of drug: The mice were grouped randomly, with 10 mice per group. 1. High dose of Embodiment 3 (5 mg/kg, per oral (P.O.), administered for 7 days); 2. middle dose of Embodiment 3 (2.5 mg/kg, P.O., administered for 7 days); 3. low dose of Embodiment 3 (1.25 mg/kg, P.O., administered for 7 days); 4. Paroxetine (3 mg/kg, P.O., administered for 7 days); and 5. physiological saline (P.O.). After 1 hour of the last drug administration, the mouse tail-hanging experiment was proceeded.

1.5.2 Experimental method: The mouse's tail (1 cm to the tail end) was taped on the wood strip higher than the platform for 5 cm and hung up for 6 minutes. The time of non-movement of the mouse for the last 5 minutes was recorded.

1.5.3 Statistic calculation: The experimental data are represented as $\overline{X} \pm SD$, and the experimental result was calculated as analysis of variance (ANOVA) by SPSS 11.5 statistic software.

1.5.4 Experimental result: Please refer to Table 1.

TABLE 1

The influence of Embodiment 3 on the time of non-movement of the mouse

| Group | Animal number | Time of non-movement (s) |
|---|---|---|
| Physiological saline (control) | 10 | 122.18 ± 45.78 |
| Paroxetine | 10 | 67.59 ± 39.09** |
| High dose of Embodiment 3 | 10 | 75.13 ± 38.26** |
| Middle dose of Embodiment 3 | 10 | 86.80 ± 48.08* |
| Low dose of Embodiment 3 | 10 | 102.36 ± 13.68 |

In comparison with the control group:
*P < 0.05, and
**P < 0.01.

Conclusion: According to the above experiment, it was found that the high and middle doses of Embodiment 3 of the present invention and Paroxetine all decreased the time of non-movement after the mouse's tail was hung. The differences were significant in comparison with the physiological group (control). Therefore, the Embodiment 3 of the present invention having anti-experimental depression function can be extrapolated.

Experiment 2: The Influence of Embodiment 3 in the Mouse Swimming by Compulsion Experiment 2.1 Experimental animals: ICR mice, male, 22.0±2 g body weight, secondary, were provided by the Experimental Animal Science Department of Capital Medical University, Beijing.

2.2 Experiment pharmaceuticals: The pharmaceutical of Embodiment 3 was provided by Beijing Wonner Biotech. Ltd. Co., and Paroxetine (Paxil) was the product of Zhong Mei Tianjin Smith Kline pharmaceuticals Co. Ltd.

2.3 Experimental equipments: Stop watch.

2.4 Dose designs: 1. High dose of Embodiment 3 (5 mg/kg/d); 2. middle dose of Embodiment 3 (2.5 mg/kg/d); and 3. low dose of Embodiment 3 (1.25 mg/kg/d).

2.5 Experimental method and result:

2.5.1 Group division and administration of drug: The mice were grouped randomly, with 10 mice per group. 1. High dose of Embodiment 3 (5 mg/kg, P.O., administered for 7 days); 2. middle dose of Embodiment 3 (2.5 mg/kg, P.O., administered for 7 days); 3. low dose of Embodiment 3 (1.25 mg/kg, P.O., administered for 7 days); 4. Paroxetine (3 mg/kg, P.O., administered for 7 days); and 5. physiological saline (P.O.).

2.5.2 Experimental method: After 1 hour of the last administration of drug, the mouse was placed in 25° C. water in the glass tank having 10 cm of the water depth and 14 cm of diameter. The accumulative time of non-movement of the mouse in the water for the last 5 minutes was recorded.

2.5.3 Statistic calculation: The experimental data are represented as $\overline{X}$±SD, and the experimental result was calculated as ANOVA by SPSS 11.5 statistic software.

2.5.4 Experimental result: Please refer to Table 2.

TABLE 2

The result of time of non-movement in the mouse swimming by compulsion experiment

| Group | Animal number | Decreased temperature (° C.) |
|---|---|---|
| Physiological saline (control) | 10 | 127.53 ± 41.80 |
| Paroxetine | 10 | 83.42 ± 40.71* |
| High dose of Embodiment 3 | 10 | 80.39 ± 40.89* |
| Middle dose of Embodiment 3 | 10 | 87.60 ± 43.42 |
| Low dose of Embodiment 3 | 10 | 91.05 ± 47.21 |

In comparison with the control group:
*P < 0.05, and
**P < 0.01.

Conclusion: According to the above experiment, it was found that the high doses of Embodiment 3 of the present invention and Paroxetine all decreased the time of non-movement in the mouse swimming by compulsion test. Therefore, the Embodiment 3 of the present invention having anti-experimental depression function can be extrapolated.

Industrial Usefulness:

The application scopes of the oral medicine of the present invention for treating depression lie in that:

1. the oral medicine described in the present invention for treating depression can include the pharmacologically acceptable additives;

2. the oral medicine described in the present invention for treating depression can be manufactured as the known dosage forms, such as powder, capsule, and tablet, etc.; and 3. the oral medicine described in the present invention for treating depression can be manufactured as the health food for treating depression.

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A method for extracting a cyclic adenosine monophosphate (cAMP) from jujuba fruits, comprising steps of:

(a) extracting an initially fractured jujuba fruit by a decoction process, wherein the fractured fruit is soaked in water and then the water-soaked-fractured-fruit is contacted with alcohol to obtain a first cAMP extract having a first cAMP concentration; and (b) chromatographing the first cAMP extract with a macroporous resin absorbent with aldehyde groups covering its surface to obtain a second extract having a second cAMP concentration, wherein the second cAMP concentration is higher than the first cAMP concentration.

2. The preparation method according to claim 1, further comprising the steps of:

(b1) chromatographing the first extract with an OU-2 macroporous resin absorbent with the aldehyde groups covering its surface; and (b2) chromatographing the extract obtained from the step (b1) with an ME-2 macroporous resin absorbent with the aldehyde groups covering its surface to obtain the second extract.

3. A method for extracting cyclic adenosine monophosphate (cAMP) from jujuba fruits, comprising steps of:

(a) extracting an initially fractured jujuba fruit by a decoction process, wherein the fractured fruit is soaked in water and then the water-soaked-fractured-fruit is contacted with alcohol to obtain a first cAMP extract; and (b) chromatographing the first cAMP extract with a macroporous resin absorbent with aldehyde groups covering its surface to obtain a chromatographed product having the cAMP.

* * * * *